US00PP37484P2

(12) United States Plant Patent
Rat

(10) Patent No.: US PP37,484 P2
(45) Date of Patent: Jun. 23, 2026

(54) PEONY PLANT NAMED 'RTPIV 791-28'

(50) Latin Name: ***Paeonia lactiflora* x *Paeonia lutea* hybrid**
Varietal Denomination: RTPIV 791-28

(71) Applicant: Early Morning LLC, Greendale, IN (US)

(72) Inventor: Thierry Rat, Gimont (FR)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 19/257,432

(22) Filed: Jul. 1, 2025

(51) Int. Cl.
*A01H 5/02* (2018.01)
*A01H 6/00* (2018.01)

(52) U.S. Cl.
USPC ..... Plt./316

(58) Field of Classification Search
USPC ..... Plt./316
See application file for complete search history.

*Primary Examiner* — Susan McCormick Ewoldt
(74) *Attorney, Agent, or Firm* — Weatherly IP Solutions, LLC; John E. Pritchard; James M. Weatherly

(57) ABSTRACT

A new and distinct variety of peony plant with light pink flowers with a creamy yellow shade; a medium-sized perennial herbaceous shrub with vigorous yet compact growth that is floriferous due to numerous secondary buds and that propagates very easily by root clump divisions, is disclosed.

2 Drawing Sheets

Genus and species: *Paeonia lactiflora* x *Paeonia lutea* hybrid.

Denomination: 'RTPIV 791-28'.

BACKGROUND

'RTPIV 791-28' is a new and distinct variety of *Paeonia lactiflora* x *Paeonia lutea* hybrid. 'RTPIV 791-28' originated from a controlled cross in May 2007 in Endoufielle, Occitanie, France between the *Paeonia lactiflora* female parent 'Miss América' (unpatented) and the *Paeonia lutea* male parent 'Golden Era' (unpatented).

The resulting seeds from the cross were collected, planted and evaluated in February 2008 in Endoufielle, Occitanie, France. 'RTPIV 791-28' was selected in May 2016 from the population of seedlings in France. 'RTPIV 791-28' was first asexually propagated in 2019 in Endoufielle, Occitanie, France from root clump division. 'RTPIV 791-28' has been shown to reproduce true to type in successive generations of asexual reproduction via root clump division.

SUMMARY

The following are the most outstanding and distinguishing characteristics of this new variety when grown under normal horticultural practices in France.

1. A perennial herbaceous plant with light pink flowers with a creamy yellow shade;
2. Vigorous, mid-season flowering with medium-sized, compact growth;
3. Florifous due to numerous secondary buds; and
4. Propagates easily by root clump division.

DESCRIPTION OF THE PHOTOGRAPHS

This new peony plant is illustrated by the accompanying photographs which show the plant's overall plant habit including form, foliage, and flowers. The photographs are of an eight year old plant grown outdoors in France in May 2016. The colors shown are as true as can be reasonably obtained by conventional photographic procedures.

DETAILED DESCRIPTION

Figure 1:
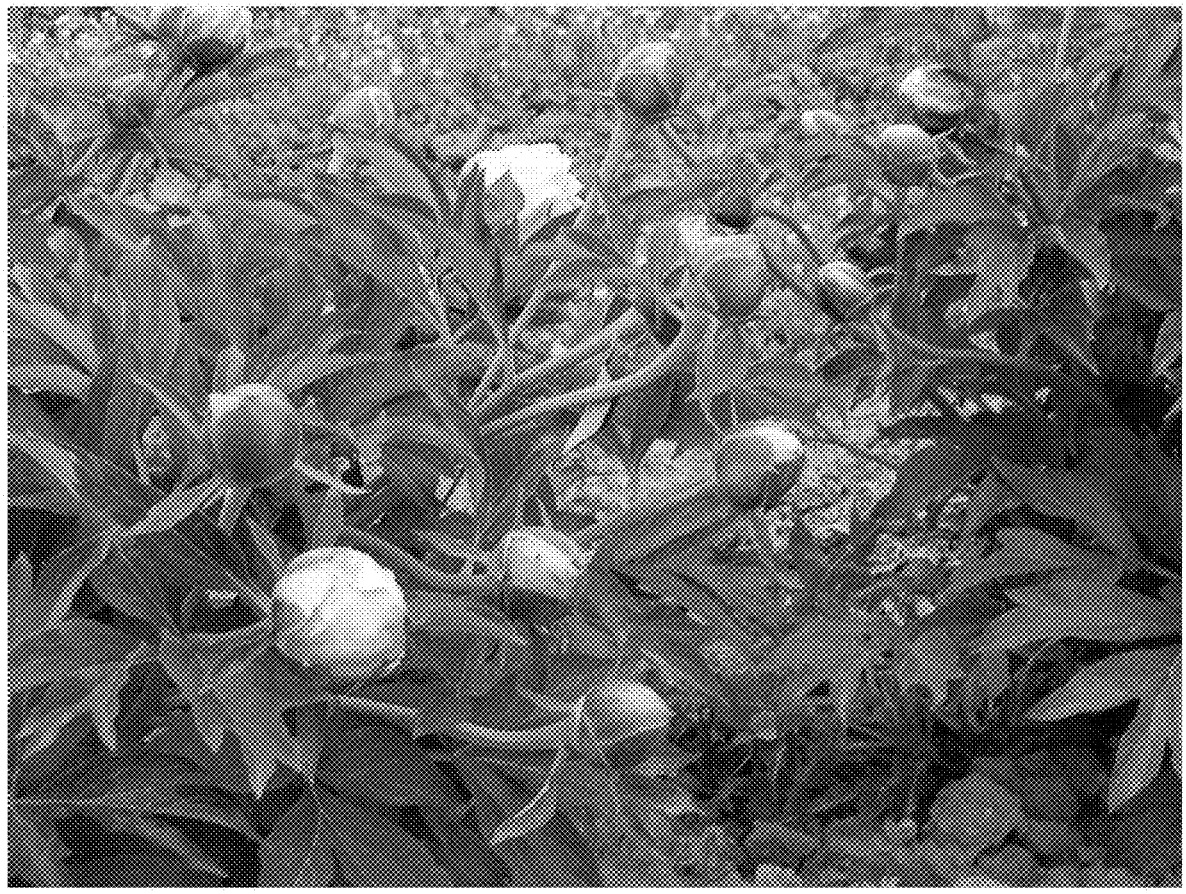
FIG. 1 shows the whole plant including flowers, buds, and the foliage of 'RTPIV 791-28'.
Figure 2:
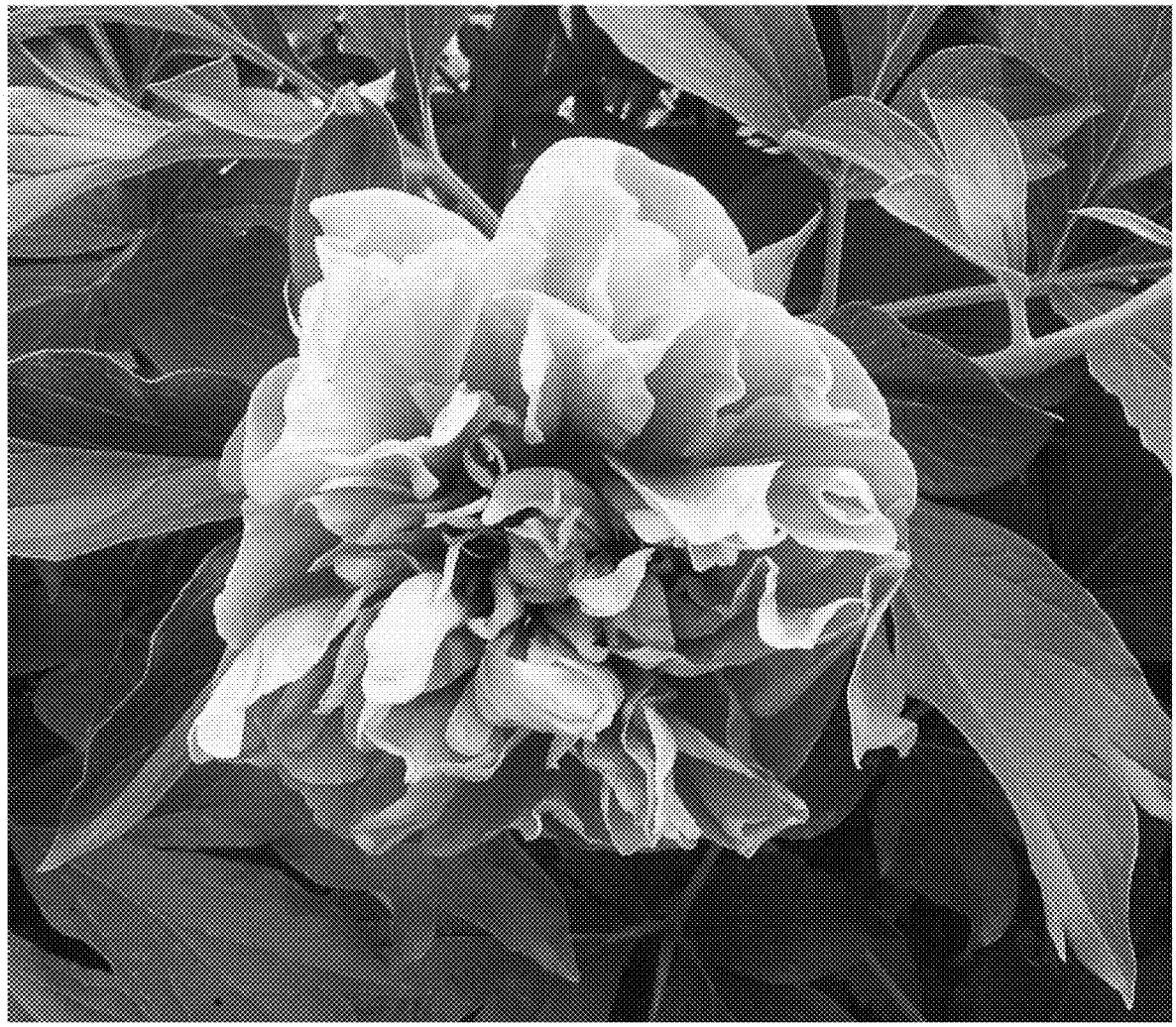
FIG. 2 shows a close-up of an individual flower of 'RTPIV 791-28'.

The following detailed descriptions set for the distinctive characteristics of 'RTPIV 791-28'. The data which define these characteristics were collected outdoors in France. The plants were eight years old when the descriptions were taken. Color references are to The Royal Horticultural Society of London (R.H.S.) Colour Chart, 2001 edition, except where general terms of ordinary dictionary significance are used.

Classification:
- *Family*.—Paeoniaceae.
- *Species*.—*Paeonia lactiflora* x *Paeonia lutea* hybrid.
- *Variety*.—'RTPIV 791-28'.

Parentage:
- *Female parent*.—*Paeonia lactiflora* female parent 'Miss America' (unpatented).
- *Male parent*.—*Paeonia lutea* male parent 'Golden Era' (unpatented).

Plant:
- *Type*.—Root clump division.
- *Root description*.—Fleshy storage root, color is RHS 165A.
- *Rooting habit*.—Freely branching storage and feeder roots.
- *Growth habit*.—Perennial herbaceous shrub; compact and symmetrically rounded; vigorous growth habit.
- *Plant height*.—50 cm to 60 cm.
- *Plant width*.—70 cm to 80 cm.

Stem:
- *Quantity of flowers per branch*.—4 to 5.
- *Length*.—50 cm to 60 cm.

*Diameter between first and* 2nd leaf.—1.08 cm.
*Internode length* (*highly variable*).—6 cm to 8 cm.
*Aspect*.—Mostly upright.
*Strength*.—Strong.
*Color*.—144C (Yellow-Green).

Leaf:
*Arrangement*.—Alternate, biternately compound with three primary leaflets further divided into second leaflets of variable number and form.
*Leaf length* (*including petiole*).—30 cm to 35 cm.
*Leaf width*.—About 25 cm.
*Leaflet length* (*central*).—16 cm to 18 cm.
*Leaflet width* (*central*).—13 cm to 26 cm.
*Leaflet shape*.—Broadly elliptical, variably incised.
*Leaflet apex*.—Broadly acuminate, often with emargination.
*Leaflet base*.—Attenuate.
*Leaflet margin*.—Entire, slightly wavy and deeply incised.
*Leaflet texture* (*both upper and lower surfaces*).—Smooth, glabrous.
*Leaflet venation pattern*.—Pinnate; reticulate.
*Leaf color*.—Upper surface: 147A (Yellow-Green). Lower surface: 191C (Yellow-Green). Venation: 145C (Yellow Green).
*Petiole*.—Length (of the 2nd leaf): About 13 cm. Diameter: 0.7 cm. Color: 145C (Yellow-Green).

Flower:
*Flower shape, arrangement and flowering habit*.—Double flower-peduncle; flowers are terminal or axillary; flower face is upright to outward; flowers are arranged above the foliage.
*Natural flower season* (*south-west France*).—Mid-May.
*Flower longevity*.—Flowers last about 8 to 12 days on the plant.
*Fragrance*.—Slight and pleasant.

Flower buds:
*Length*.—4.5 cm.
*Diameter*.—3.5 cm.
*Shape*.—Globose.
*Color*.—144A (Yellow-Green).

Flowers:
*Diameter*.—About 15.0 cm.
*Depth*.—6.0 cm.
*Petals*.—Quantity (main flower): About 40 petals. Length: 7.0 cm. Width: 5.0 cm. Shape: Rounded. Apex: Slightly emarginate. Margin: Entire to slightly sinuate. Texture, upper and lower surfaces: Smooth, glabrous. Color: 49B (Light pink) and 9D (Yellow) on the upper surface. Flare: 60A (Red-Purple), large flare over 50% of the petal surface.
*Petaloids*.—Absent.
*Sepals*.—Quantity: 2 small and 3 large. Length: Small are 2.0 cm and large are 3.5 cm. Width (outer): Small are 0.5 cm and large are 3.0 cm. Shape: Obcordate to obovate. Apex: Mucronate. Margin: Entire to slightly emarginate. Texture: Smooth, glabrous (upper and lower surfaces). Color: 144B (Yellow-Green) at the base with the remaining surface 183C (Greyed-Purple).
*Peduncles* (*main bud*).—Length: 10 cm to 20 cm. Diameter: 0.6 cm. Strength: Strong. Texture: Smooth, slightly fluffy. Color: 144D (Yellow-Green).

Reproductive organs:
*Stamen*.—Quantity per flower: Few, variable. Filament length: About 1.5 cm. Filament color: 60A (Red-Purple). Anther: Absent.
*Pistil*.—Quantity per flower: 4 tall pistils plus 2 to 3 smaller ones in the middle. Length: Small are 0.5 cm and large are 1.5 cm. Stigma shape: Claw-shaped, convex. Stigma color: 145C (Yellow-Green). Ovary color: 145C (Yellow-Green). Ovary appearance: Fluffy.
*Floral disk*.—Strength: Strong. Diameter: 3.0 cm. Color: 144D (Yellow-Green).

Fruit and seed set: Seed production has not been observed.
Disease and insect resistance: None observed.
Temperature tolerance: Hardy like other intersectional hybrid peonies.

COMPARISON WITH PARENTAL AND COMMERCIAL LINES

Table 1 shows a comparison of differences between 'RTPIV 791-28' and both parental lines.

TABLE 1

Comparison with Parental Lines

| Characteristic | 'RTPIV 791-28' | Female parent 'Miss America' | Male parent 'Golden Era' |
|---|---|---|---|
| Flower color | Light pink with a creamy yellow shade | Pure white | Yellow-Orange |

Table 2 shows a comparison of the differences between 'RTPIV 791-28' and the commercial peony variety 'Coral Charm' (U.S. Plant Pat. No. 4,247).

TABLE 2

Comparison with Commercial Line

| Characteristic | 'RTPIV 791-28' | 'Coral Charm' |
|---|---|---|
| Flower color | Light pink with a creamy yellow shade | Coral orange |

Table 3 below shows a comparison of the differences between 'RTPIV 791-28' and the commercial peony variety 'RTPIV 791-38' (U.S. Plant Pat. No. 26,909).

TABLE 3

Comparison with Commercial Line

| Characteristic | 'RTPIV 791-28' | 'RTPIV 791-38' |
|---|---|---|
| Plant habit | Shorter and more floriferous than 'RTPIV 791-38' | Taller and less floriferous than 'RTPIV 791-28' |

I claim:

1. A new and distinct variety of peony plant designated 'RTPIV 791-28' as illustrated and described herein.

* * * * *